(12) United States Patent
Inoue et al.

(10) Patent No.: US 6,852,281 B2
(45) Date of Patent: Feb. 8, 2005

(54) GAS INDICATOR AND GAS SENSOR SHEET

(75) Inventors: Hiroshi Inoue, Higashiosaka (JP);
Satoshi Maruyama, Yao (JP);
Masahiro Yasunaga, Osaka (JP)

(73) Assignee: Sakura Color Products Corporation, Osaka (JP)

( * ) Notice: Subject to any disclaimer, the term of this patent is extended or adjusted under 35 U.S.C. 154(b) by 205 days.

(21) Appl. No.: 09/897,659

(22) Filed: Jun. 29, 2001

(65) Prior Publication Data

US 2002/0083883 A1 Jul. 4, 2002

(30) Foreign Application Priority Data

Jun. 30, 2000 (JP) .......................................... 2000-197766
Aug. 29, 2000 (JP) .......................................... 2000-259716
Jan. 30, 2001 (JP) .......................................... 2001-22208

(51) Int. Cl.$^7$ ........................ G01N 33/00; G01N 33/497
(52) U.S. Cl. ............................. 422/58; 422/61; 422/85; 422/87; 436/164; 73/23.2
(58) Field of Search .............................. 422/56, 58, 61, 422/83, 85–87; 436/164, 166; 73/23.2, 23.3, 335.01

(56) References Cited

U.S. PATENT DOCUMENTS

| 4,485,665 A | * | 12/1984 | Norman ...................... 73/29.01 |
| 4,904,449 A | * | 2/1990 | Heckmann .................... 422/87 |
| 6,117,685 A | * | 9/2000 | Omatsu et al. ............. 436/135 |

FOREIGN PATENT DOCUMENTS

| JP | 10-316910 | 12/1998 |
| JP | 11-83834 | 3/1999 |
| JP | 11-140360 | 5/1999 |

* cited by examiner

*Primary Examiner*—Lyle A. Alexander
(74) *Attorney, Agent, or Firm*—Knobbe, Martens Olson & Bear LLP

(57) ABSTRACT

The invention designed to provide a gas indicator which can be applied over a broad range of gas concentration from a low concentration gas to a high concentration gas is concerned with a gas indicator comprising a housing and a change-color gas sensor element with which the housing is loaded, the housing internally defining a gas passage space extending from its gate through its bottom with the area of its cross-section parallel to the plane of the gate being progressively reduced from the gate to the bottom.

23 Claims, 13 Drawing Sheets (b)

C-C sectional figure

Shaded area: printing portion

Shaded area: printing portion

A-A sectional figure

B-B sectional figure

C-C sectional figure (c-2)

(b)
(a)

(c-1)

A-A sectional figure

B-B sectional figure

A-A sectional figure

B-B sectional figure

C-C sectional figure

GAS INDICATOR AND GAS SENSOR SHEET

FIELD OF THE INVENTION

The present invention relates to gas indicators and gas sensor sheets.

BACKGROUND OF THE INVENTION

A large number of methods has been proposed for the detection of gases. Particularly the detection technology using a small-sized indicator is a current focus of attention in the light of Its convenience in use and economic advantage. For example, there are known high-sensitivity gas indicators (Japanese Unexamined Patent Publication H8-122318 and H7-49342) each comprising a gas indicator body formed in a generally plate-like configuration and internally defining a passageway for admitting a specific gas to be detected and an indication layer adapted to react with said specific gas to undergo change in shade as affixed along said passageway to the inside wall of the body, said gas indicator body having a gate having a predetermined sectional area through which said specific gas may immediately come into contact with the indicator body and said indication layer being formed in the zone of said gate.

However, this prior art has the drawback that when a gas of low diffusibility is present only in a low concentration, its CT value (gas concentration×exposure time) can hardly be detected. This problem can be resolved by increasing the gas detection sensitivity. However, if the gas detection sensitivity is increased, the whole indicator undergoes a change in color instantly when exposed to a high concentration of gas so that the new problem occurs that its CT value can hardly be detected.

Thus, the development of a gas indicator applicable to both high and low gas concentrations was awaited but such an indicator remained to be developed and implemented yet.

It is, therefore, a primary object of the invention to provide a gas indicator applicable over a broad range of gas concentrations from a gas of low concentration to a gas of high concentration.

SUMMARY OF THE INVENTION

The inventor of the present invention did much research in view of the above drawback of the prior art and found that the above object can be accomplished by using an indicator having a defined construction. The present invention has been developed on the basis of the above finding.

The present invention, therefore, relates to the following gas indicators and gas sensor sheets.
1. A gas indicator comprising a housing and a change-color gas sensor element with which the housing Is loaded, said housing internally defining a gas passage space extending from a gate thereof to a bottom thereof and having a shape such that the area of its cross-section parallel to the plane of said gate being progressively reduced from said gate to said bottom.
2. The gas indicator according to the above paragraph 1 wherein the housing is provided with a transparent window through which a change in shade of the change-color gas sensor element can be ascertained from outside the Indicator.
3. The gas indicator according to the above paragraph 1 wherein the housing is a plate-shaped casing.
4. The gas indicator according to the above paragraph 1 wherein the gate of the housing is formed with a notch.
5. The gas indicator according to the above paragraph 1 wherein the change-color gas sensor element has a change-color layer formed from a gas sensor ink on a substrate
6. The gas indicator according to the above paragraph 5 wherein the gas sensor sheet is supported by a sheet hold means provided internally of the housing.
7. The gas indicator according to the above paragraph 6 wherein the sheet holding means is comprised of one or more than one projection extending from the inside wall of the housing.
8. The gas indicator according to the above paragraph 6 wherein the sheet holding means is comprised of two or more projections extending from the inside wall of the housing, said projections being disposed in mutually opposed relation to hold the gas sensor sheet therebetween.
9. The gas indicator according to the above paragraph 6 wherein the apices of the mutually opposed projections are displaced from each other, with the apex of one projection being situated on the base side of the apex of the other projection and the gas sensor sheet being supported between the displaced apices.
10. The gas indicator according to the above paragraph 6 wherein one of the mutually opposed projections is shorter than the other projection so that the gas sensor sheet may be supported in the vicinity of the lower inside wall of the housing.
11. The gas indicator according to the above paragraph 6 wherein the projection is a plate-like element extending from the bottom toward the gate of the housing.
12. The gas indicator according to the above paragraph 6 wherein the projection is a plate-like element extending from the bottom toward the gate of the housing, said plate-like projection being secured to the lateral inside wall of the housing as well.
13. The gas Indicator according to the above paragraph 6 wherein one inside wall of the housing is provided with a couple of first projections and the opposite inside wall of the housing Is provided with one second projection, with (a) the apices of said first projections being situated on the base side of the apex of said second projection and (b) said first projections being shorter than said second projection so that the gas sensor sheet is supported in the vicinity of that inside wall of the housing which Is provided with said first projections, (a) said second projection being located where it presses that part of the gas sensor sheet which is intermediate between those parts pressed by said couple of first projections, and (e) each of said first and second projections being shaped like a plate extending from the bottom wall toward the gate of the housing.
14. The gas indicator according to the above paragraph 6 wherein the change-color layer of the gas sensor sheet is formed in a stripe pattern which is parallel to the cross-section of the gate.
15. The gas indicator according to the above paragraph 5 wherein the gas sensor ink contains an anthraquinone dye having at least one kind of amino group, namely primary amino and/or secondary amino.
16. The gas indicator according to the above paragraph 5 wherein the gas sensor ink further contains a cationic surfactant of the quaternary ammonium salt type.
17. The gas indicator according to the above paragraph 16 wherein the cationic surfactant of the quaternary ammonium salt type is an alkyltrimethylammonium salt.
18. The gas indicator according to the above paragraph 5 wherein the gas sensor ink further contains an extender.

19. The gas indicator according to the above paragraph 5 wherein the gas sensor Ink further contains a binder.
20. The gas indicator according to the above paragraph 5 wherein the gas sensor ink further contains a color component which is not altered in shade in an ozone-containing atmosphere.
21. A gas sensor sheet comprising a substrate sheet and a change-color layer formed from a gas sensor ink on said substrate, said change-color layer being formed in a stripe pattern.
22. The gas sensor sheet according to the above paragraph 21 wherein the gas sensor ink contains an anthraquinone dye having at least one kind of amino group, namely primary amino and/or secondary amino.
23. The gas sensor sheet according to the above paragraph 21 wherein the gas sensor ink further contains a cationic surfactant of the quaternary ammonium salt type.
24. The gas sensor sheet according to the above paragraph 23 wherein the cationic surfactant of the quaternary ammonium salt type is an alkyltrimethylammonium salt.
25. The gas sensor sheet according to the above paragraph 21 wherein the gas sensor ink further contains an extender.
26. The gas sensor sheet according to the above paragraph 21 wherein the gas sensor ink further contains a binder.
27. The gas sensor sheet according to the above paragraph 21 wherein the gas sensor ink further contains a color component which is not altered in shade in an ozone-containing atmosphere.
28. A method of determining the concentration of a gas which comprises disposing the gas indicator of above paragraph 1 in a given atmosphere and determining the CT value from the color difference or color change area resulting from a change in shade of the change-color layer of the gas sensor sheet.

BRIEF DESCRIPTION OF THE DRAWINGS

FIG. 1(a) is a perspective view showing the gas indicator prior to loading with a gas sensor sheet. FIG. 1(b) shows a plate-like housing loaded with a sheet-like change-color sensor element (gas sensor sheet).

FIG. 2(a) is a plan view and FIG. 2(b) is a side elevation view.

FIG. 3(a) is a plan view and FIG. 3(b) is a side elevation view.

FIG. 4(a) is a side elevation view, FIG. 4(b) Is a plan view, and FIGS. 4(c-1) and (c-2) are cross-section views.

FIG. 11(a) is a side elevation view, FIG. 11 (b) is a plan view, and FIGS. 11(c-1) and (c-2) are cross-section views.

FIG. 15(b) is a plan view, and FIGS. 15(c-1) and (c-2) are cross-section views.

FIG. 18(a) is a side-elevation view, FIG. 18(b) is a plan view, and FIGS. 18(c-1) and (c-2) are cross-section views.

DETAILED DESCRIPTION OF THE INVENTION

The gas indicator of the present invention is a gas sensor comprising a housing and a change-color gas sensor element with which the housing is loaded, said housing having a gas passage space extending from an open end (gate) thereof to its bottom end and having a cross-sectional area parallel to said gate diminishing progressively from the gate to the bottom wall.

The housing mentioned above is not particularly restricted inasmuch as it has a space for accepting said change-color gas sensor element and has an opening (gate).

The material for the housing is not restricted but can be judiciously selected according to the kind of gas to be detected and the intended use of the end product apparatus, among other variables. For example, the housing may be made of any known material such as resin, glass or metal. Particularly, for allowing observation of the change in shade of the change-color sensor element from outside of the apparatus, the housing may be made, either in part or as a whole, of a transparent material.

The shape of the housing is not particularly restricted inasmuch as the area of its cross-section parallel to the opening (gate area) is diminishing progressively from the gate to the bottom. Thus, the present invention employs a structure such that the space in the housing is progressively reduced from the gate to the bottom.

An exemplary housing having such a shape is shown in FIG. 1(a). This housing comprises an opening (gate) (1) for admitting the gas to be detected, a bottom wall (2) which is farthest from the gate, a lower side wall (3), an upper side wall (4), and two lateral side walls (5), (6). The housing is so designed that its width is progressly reduced toward the bottom wall. Thus, it is so designed that the area (A) of the cross-section parallel to the gate (plane of the gate) is progressively diminishing toward the bottom. It is particularly preferable that the above cross-sectional area be continuously diminishing toward the bottom wall. The gradient of said sectional area can be judiciously selected according to the kind of gas to be detected, among other variables, but is generally such that the gate area (sectional area) Is not less than 1.5 times as large, preferably not less than 2 times as large, more preferably not less than 3 times as large, as the bottom area (sectional area).

Figure 2:
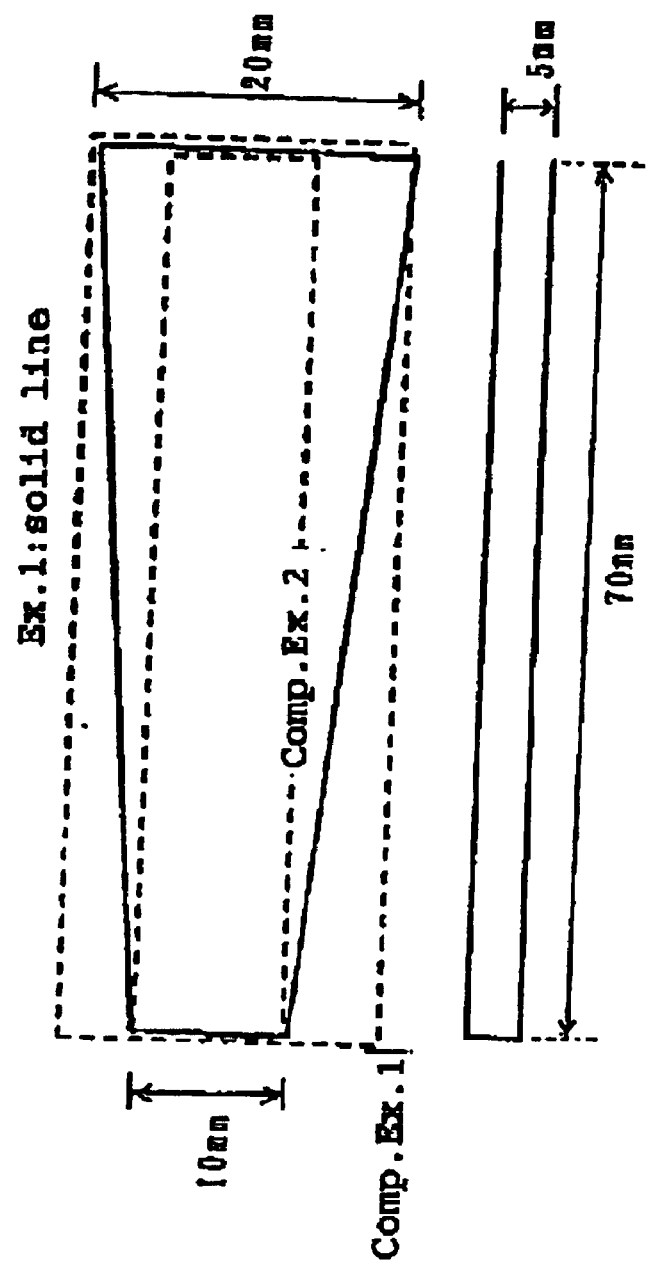
FIG. 2 is a diagrammatic representation of the configurations of housings used in Examples (solid lines) and Comparative Example (dotted lines) (unit dimension: mm; the same applies hereunder).

The housing for use in the present invention preferably has a plate-like configuration. For example, a housing in the form of a thin plate about 5 mm thick as illustrated (in solid lines) in FIG. 2 can be used with advantage. This housing is progressively reduced in width from the gate (20 mm wide) to the bottom wall which is 10 mm wide and consequently the sectional area of the housing is diminishing gradually from the gate to the bottom. When such a plate-like housing is adopted, its length (distance between gate and bottom) may be freely selected but generally is preferably not less than 1.5 times greater, preferably not less than 2 times greater, than the width of the gate. For example, assuming that the gate width is 20 mm, the above-mentioned length is preferably not less than 40 mm as shown in FIG. 2 (70 mm long in FIG. 2).

The above housing, in the condition loaded with the change-color gas sensor element, has a gas passage space extending from the gate to the bottom of the housing. The design of this gas passage space is not particularly restricted inasmuch as the gas may flow from the gate to the bottom of the housing. For example, FIG. 1(b) shows the plate-like housing loaded with a sheet-like change-color gas sensor element (gas sensor sheet). When the plate-like housing is loaded with a sheet-like change-color gas sensor element (7) which Is generally of the same configuration as the lower side wall (3) or upper side wall (4) of the housing but of low profile as compared with the thickness (inside thickness) of the housing, with said sensor element (7) disposed in contact with said lower side wall (3), a space (8) is formed adjoining to said upper side wall (4) within the housing as shown in FIG. 1(b). Through this space, the gas entering the gate may flow toward the bottom wall (2).

Figure 3:
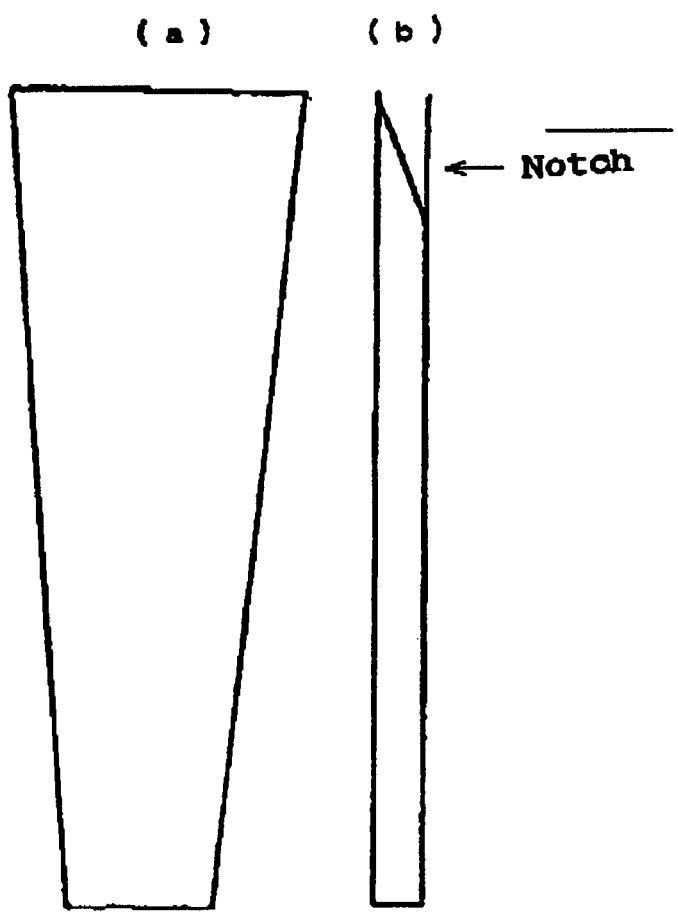
FIG. 3 is a diagrammatic representation of an embodiment of the invention in which the side wall in the gate zone of a plate-like housing is provided with a notch.

In the present invention, the gate of the housing may be formed with a notch. Thus, there may be adopted the structure illustrated in FIG. 3, where the gate of the plate-like housing is obliquely notched (as viewed from the lateral side). By this arrangement, the accuracy of detection of a low-concentration gas or a low CT value can be enhanced.

In order that the change in shade of the change-color gas sensor element may be visually recognized from outside the housing, the housing is preferably provided with a transparent window or made throughout of a transparent material. The transparent material that can be used is not particularly restricted but includes not only clear resins such as acrylic resins but other known transparent materials inclusive of glass. When the housing is totally made of an opaque material, the change in shade of the change-color sensor element can be recognized by withdrawing the element from the housing and inspecting it.

When the gas sensor sheet described hereunder is used as the gas sensor element, the sensor sheet is preferably supported by a sheet holding means provided within the housing.

The sheet hold means is not restricted in construction inasmuch as the gas sensor sheet can be supported thereby but is preferably comprised of one or more than one projection disposed on the inside wall of the housing. The shape, number of units, and location of said projection are not particularly restricted inasmuch as the gas sensor sheet can be secured in position by the structure and may be judiciously determined according to the shape of the housing and the type of gas sensor sheet, among other variables.

The preferred projection is a plate-shaped projection extending from the inside bottom wall of the housing, which is farthest from the gate, toward said gate. Moreover, the projection is preferably in direct contact with said inside wall of the bottom of the housing which is farthest from the gate.

The construction of the sheet hold means may for example be such that the gas sensor sheet is sandwiched between a single projection and the inside wall of the housing or such that the gas sensor sheet is sandwiched between two or more projections.

It is particularly preferable that the gas sensor sheet be supported by at least two projections provided on the inside wall in mutually opposed relation. For example, it is preferably so arranged that the apices of opposed projections are displaced from each other, with the apex of one projection being situated on the base side of the apex of the other projection, so that the gas sensor sheet may be held between the mutually displaced apices. Thus, the gas sensor sheet is preferably secured in position by causing the sheet to be pressed against by at least two projections from above and below.

When the sensor sheet is supported by mutually opposed projections, one of the opposed projections is shorter than the other so that the supported position of the gas sensor sheet will be close to the inside wall of the housing. In this manner, the gas sensor sheet can be more securely supported on the inside wall of the housing The supported position (fixing position) of the gas sensor sheet is not particularly restricted. Particularly from the standpoint of the ease of loading and unloading with the gas sensor sheet, the sheet is preferably supported in the vicinity of the bottom wall farthest from the gate of the gas indicator.

The gas indicator as one preferred embodiment of the invention is described below. Thus, one inside wall of the housing is provided with a couple of first projections and the opposing inside wall of the housing is provided with one second projection, with (a) the apices of said couple of first projections being situated on the base side of the apex of said second projection. (b) said first projections being shorter than said second projection so that the gas sensor sheet is supported in the vicinity of that inside wall of the housing which is provided with said first projections, (c) said second projection being disposed where it can press that part of the gas sensor sheet which is intermediate between the points pressed by said couple of first projections, and (d) each of said first and second projections being shaped like a plate extending from the bottom wall to the gate of the housing.

Figure 11:
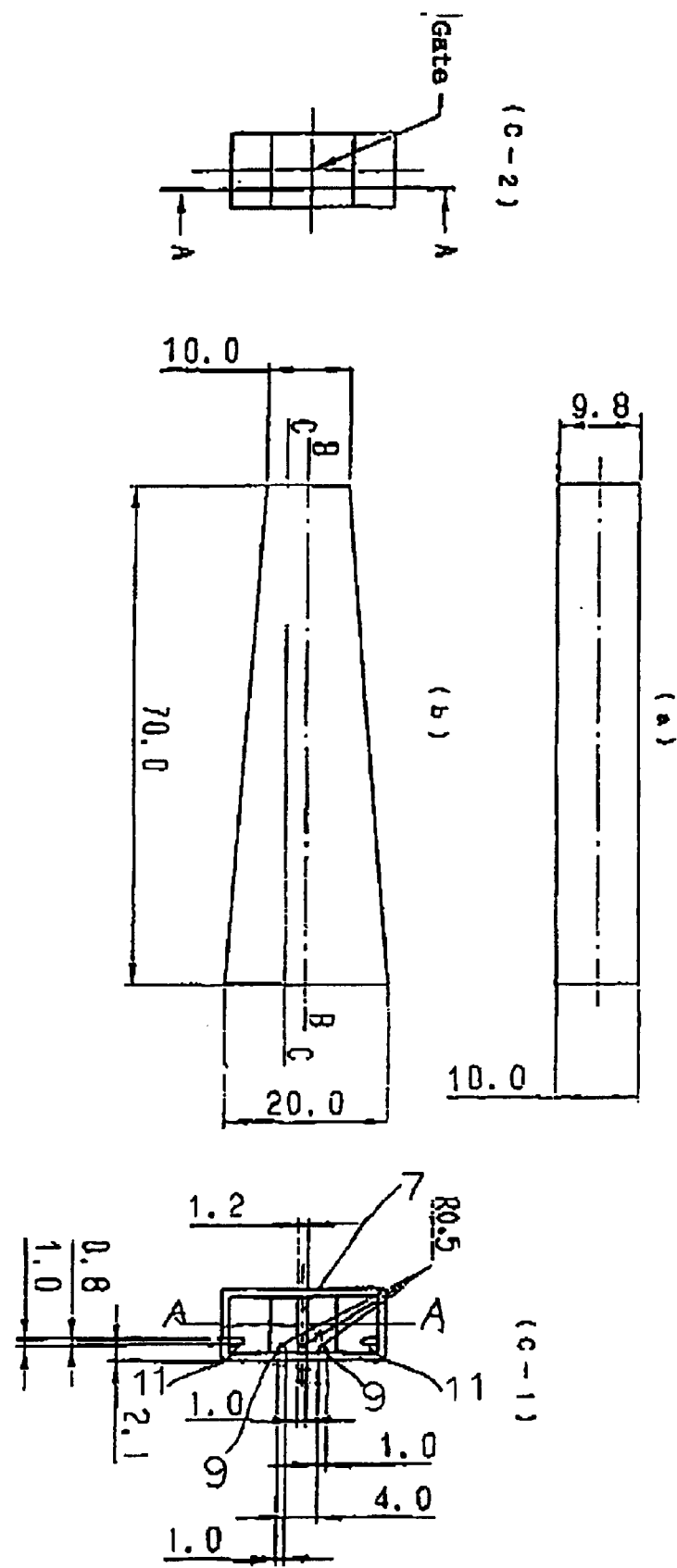
FIG. 11 is a diagram showing a gas indicator of the invention.

Furthermore, as illustrated In FIG. 11, additional projections may be disposed on lateral sides. Thus, in FIG. 11, a third projection (11) is disposed on each of the lateral walls of the housing in addition to the projections disposed on said first projections (9). (9) and second projection (7). In the embodiment illustrated in FIG. 11, the third projections help to support the gas sensor sheet more securely against the lower side wall of the housing.

As the housing is loaded with the change-color gas sensor element, the element defines a gas passage space within the housing from the gate to the bottom wall. The configuration of the gas passage space is not particularly restricted but can be judiciously selected according to the type of apparatus and the kind of gas to be detected, among other factors. When a plate-like housing having the low profile shown in FIG. 2 (solid lines), for Instance, is employed, a change-color gas sensor element having a flat shape generally identical or similar to that of the housing is used and the housing is loaded with said sensor element in such a manner that the sensor element will be held in contact with the lower inside wall of the housing to leave a clearance between the upper inside wall of the housing and the sensor element, whereby said gas passage space is formed.

In the present invention, a gas sensor sheet having a change-color layer formed from a gas sensor ink on a substrate can be used with advantage as said change-color gas sensor element. The substrate is not particularly restricted but may be made of any of such materials as metal, metal alloy, wood, paper, ceramics, glass, plastics fabrics (nonwoven cloth, woven cloth, or other fibrous sheet) and a composite of such materials. In the present invention, paper (Kent paper), for instance, can be used with particular advantage.

The gas sensor ink mentioned above can be judiciously selected from among various known inks according to the kind of gas to be detected. For the detection of ozone gas, for instance, an ozone gas sensor sheet comprising a substrate sheet and, as constructed thereon, a change-color layer made from an ozone gas sensor ink (change-color ink) can be employed. Furthermore, as the gas sensor sheet, a known sheet or a commercial sheet can be used The configuration of the gas sensor sheet (substrate) is not restricted, either, but can be freely selected according to the shape of the gas indicator, among other variables. For example, when the gas indicator is a plate-shaped one (one having a low profile), a gas sensor sheet having a configuration generally corresponding to the plan view of the gas indicator can be used with advantage.

Furthermore, when a gas sensor sheet is used, the change-color layer may be formed only on part of the surface of the substrate or all over the surface. It is particularly preferable to use a gas sensor sheet comprising a substrate and, as formed in a stripe pattern thereon, a change-color layer made from a change-color ink (the gas sensor sheet of the invention). For example, in FIG. 8, a stripe change-color layer structure consisting of four discrete change-color layers formed In a pattern of stripes at generally equal pitches can be employed. The size of each constituent change-color layer, the interval between change-color layers, and the number of change-color layers can be liberally selected according to the kind of gas to be detected, the form of the gas indicator, and the objective of gas detection, among other variables. In the area or areas where no change-color layer is formed, the substrate may be left exposed or an ink layer may be formed from a non-change-color ink (for example, a commercial ordinary color ink).

The change-color layer can be constructed by the known printing techniques such as silk screen printing, gravure printing, offset printing, relief printing, flexographic printing and so forth. Moreover, the layer may also be formed by dipping the substrate in an ozone sensor ink. This method is especially useful for ink-permeable substrates such as paper, nonwoven cloth and the like. The thickness of the change-color layer, non-change-color layer and overcoat layer can be liberally selected according to the kind of material for each layer, the intended use of the gas indicator, and other factors.

When the gas to be detected is ozone, the gas sensor ink for use in the invention is preferably an ozone sensor ink containing an anthraquinone dye having at least one kind of amino group, i.e. primary amino and/or secondary amino. By using such an ink, ozone gas can be detected with high sensitivity.

The above-mentioned anthraquinone dye is not particularly restricted insofar as it contains an anthraquinone nucleus and has a primary amino group and/or a secondary amino group, and, as such, known anthraquinone disperse dyes can also be used. Two or more amino groups may be present and may be the same or different.

As examples of said anthraquinone dye, there can be mentioned 1,4-diaminoanthraquinone (C. I. Disperse Violet 1), 1-amino-4-hydroxy-2-methoxyanthraquinone (C. I. Disperse Red 4), 1-amino-4-methylaminoanthraquinone (C. I. Disperse Violet 4), 1,4-diamino-2-methoxyanthraquinone (C. I. Disperse Red 11). 1-amino-2-methylanthraquinone (C. I. Disperse Orange 11). 1-amino-4-hydroxyanthraquinone (C. I. Disperse Red 15), 1,4,5,8-tetraaminoanthraquinone (C. I. Disperse Blue 1), 1,4-diamino-5-nitroanthraquinone (C. I. Disperse Violet 8) and so forth (C. I. Generic Names in parentheses). Aside from the above dyes, those dyes known as C. I. Solvent Blue 14, C. I. Solvent Blue 63, C. I. Solvent Violet 13, C. I. Solvent Violet 14, C. I. Solvent Red 52, C. I. Solvent Red 114, C. I. Vat Blue 21, C. I. Vat Blue 30, C. I. Vat Violet 15, C. I. Vat Violet 17, C. I. Vat Red 19, C. I. Vat Red 28, C. I. Acid Blue 23, C. I. Acid Blue 80, C. I. Acid Violet 43, C. I. Acid Violet 48, C. I. Acid Red 81, C. I. Acid-Red 83, C. I. Reactive Blue 4. C. I. Reactive Blue 19, C. I. Disperse Blue 7. etc. can also be employed. These anthraquinone dyes can be used each independently or in a combination of two or more species. Among those anthraquinone dyes, C. I. Disperse Blue 7 and C. I. Disperse Violet 1 are especially preferred. In the present invention, the sensitivity of ozone detection can be controlled by varying the kinds (molecular structures etc.) of anthraquinone dyes.

The anthraquinone dye content can be judiciously selected according to the kind of anthraquinone dye selected but may usually be about 0.05~10 weight %, preferably 0.05~5 weight %, more preferably 0.1~1 weight %.

In the present invention, a cationic surfactant of the quaternary ammonium salt type is preferably incorporated In the ink containing said anthraquinone dye.

The cationic surfactant of the quaternary ammonium salt type (hereinafter referred to sometimes briefly as "cationic surfactant"), is not particularly restricted. Usually, alkylammonium salts are used and commercial products may also be employed. Furthermore, these may be used each independently or in a combination of two or more species. In the present invention, a still higher ozone detection sensitivity is attained by using such a cationic surfactant in combination with said anthraquinone dye.

The preferred, among such cationic surfactants, are alkyltrimethylammonium salts and dialkyldimethylammonium salts. Specifically, there can be mentioned cocoalkyltrimethylammonium chloride, tallow alkyltrimethylammonium chloride, behenyltrimethylammonium chloride, hexadecyltrimethylammonium chloride, lauryltrimethylammonium chloride, octadecyltrimethylammonium chloride, dioctyldimethylammonium chloride, distearyldimethylammonium chloride, alkylbenzyldimethylammonium chloride and so forth. Particularly preferred is lauryltrimethylammonium chloride.

The level of addition of the cationic surfactant can be judiciously selected according to the kind of surfactant used and may for example be generally about 0.2~30 weight %, preferably about 0.5~10 weight %.

In the above-mentioned ink, the known formulating ingredients for inks, such as the resinous binder, extender, solvent, etc., can be incorporated in suitable amounts where necessary.

The resinous binder can be liberally selected according to the type of substrate used. For example, the known resinous ingredients for writing or printing ink compositions can be used as they are. Specifically, there can be mentioned maleic acid resins, amide resins, ketone resins, alkylphenol resins, rosin-modified resins, polyvinyl butyral, polyvinylpyrrolidone, cellulosic resins, acrylic resins, vinyl acetate resins and so forth.

The level of the resinous binder can be judiciously selected according to the kind of binder used but may for example be generally not more than 50 weight %, preferably 5~35 weight %.

The extender is not particularly restricted but includes bentonite, active clay, aluminum oxide and silica gel, among others. Aside from these, the various substances generally known as extender pigments can also be employed. Among these, porous extenders are preferred, silica gel being particularly preferred. By adding such an extender, chiefly the detection sensitivity can be improved.

The level of the extender can be judiciously selected according to the kind of extender used and may for example be generally about 1~30 weight %, preferably 2~20 weight %.

Furthermore, in the present invention, said ozone sensor ink may contain a color component which does not undergo change in shade in an ozone-containing atmosphere. When such a color component is contained, the change in shade of the change-color layer may be expected to be easier to recognize visually. Such color component is not restricted but may for example be a normal color ink or an oil-soluble dye or pigment.

The level of said color component can be liberally selected according to the kind of color component but may for example be generally about 0.05~10 weight %, preferably about 0.1~3 weight %.

The solvent may be any solvent that is usually contained in printing and writing ink compositions. For example, various solvents including alcohols, esters, ethers, ketones and hydrocarbons can be selectively employed according to the solubilities of the dye and resinous binder to be used. The solvent can be used to make up for the balance after formulation of said various ingredients.

These ingredients can be formulated at one time or serially and blended evenly using a known stirring machine such as a homogenizer, a dissolver or the like. A typical procedure may comprise formulating the anthraquinone dye, cationic surfactant, resinous binder, extender, etc. serially with the solvent and blending them under stirring.

The apparatus of the invention, when installed in (exposed to) an atmosphere containing the gas to be detected, detects the gas concentration and CT value (gas concentration×exposure time) accurately and rapidly. The gas to be detected is not restricted but substantially any kind of gas may be detected by judicious choice of the change-color sensor element. For example, by using a change-color sensor element incorporating said ozone sensor ink, ozone can be detected with advantage.

In the present invention, based on known data on the relationship of CT to color difference (ΔE) or the relationship of CT to color change area, for instance, the gas concentration and CT value can be determined qualitatively or quantitatively from the actually detected color difference or color change area. For example, when the housing is provided with graduations corresponding to CT values along the change-color layer of the apparatus of the invention, the CT value can be quantitatively determined according to the size of color change area of the change-color layer. Furthermore, based on the CT value found, the gas concentration or the exposure time can be determined quantitatively or qualitatively.

Since the apparatus of the invention is so constructed that said space is diminishing gradually from the gate to the bottom, a clear-cut indication of the change in shade of the color-change region is assured even In an atmosphere containing only a low concentration of the gas to be detected. Therefore, a gas over a broad concentration range from a low concentration to a high concentration or over a broad range of CT value from a low CT value to a high CT value can be detected with a single apparatus. Particularly because the apparatus of the invention provides a clear-cut color change indication, it is optimal for the determination of CT values.

When the gas to be detected is ozone and the change-color layer is constituted of an anthraquinone dye having at least one kind of amino group, i.e. a primary amino and/or secondary amino, the indicator reacts with ozone effectively even in substantially anhydrous condition to express an improved detection accuracy (selectivity), sensitivity and stability, thus facilitating the detection of ozone even with the unaided eye.

The gas indicator according to the Invention comprises a gas indicator housing loaded with a gas sensor sheet. The gas sensor sheet is supported securely in position by the sheet hold means of the apparatus.

The gas indicator of the invention, when installed in an atmosphere containing the gas to be detected, detects the gas from the change in shade (degree of change) of the change-color layer of the gas sensor sheet. By providing the gas sensor sheet or the gas indicator housing with graduations in advance, a quantitative gas detection is made feasible.

Figure 1:
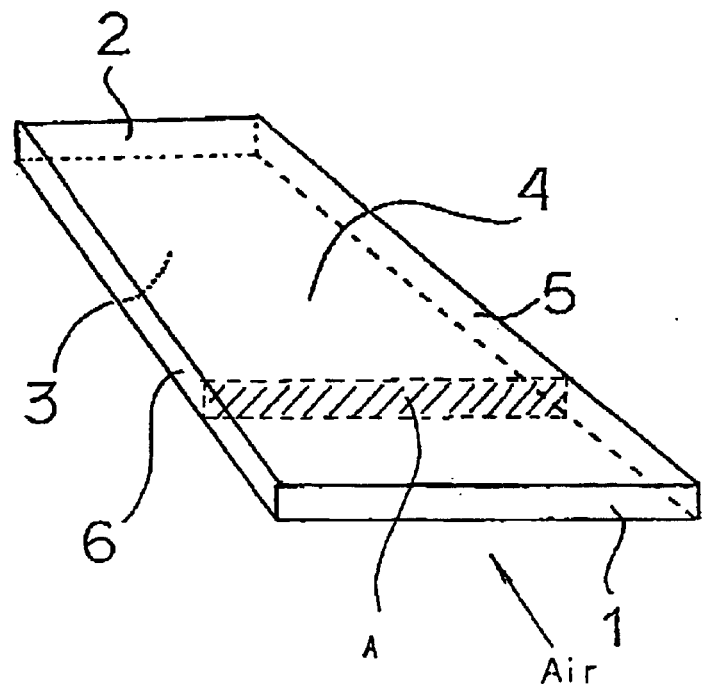
FIG. 1 is a perspective view showing a gas indicator embodying the present invention.
Figure 1:
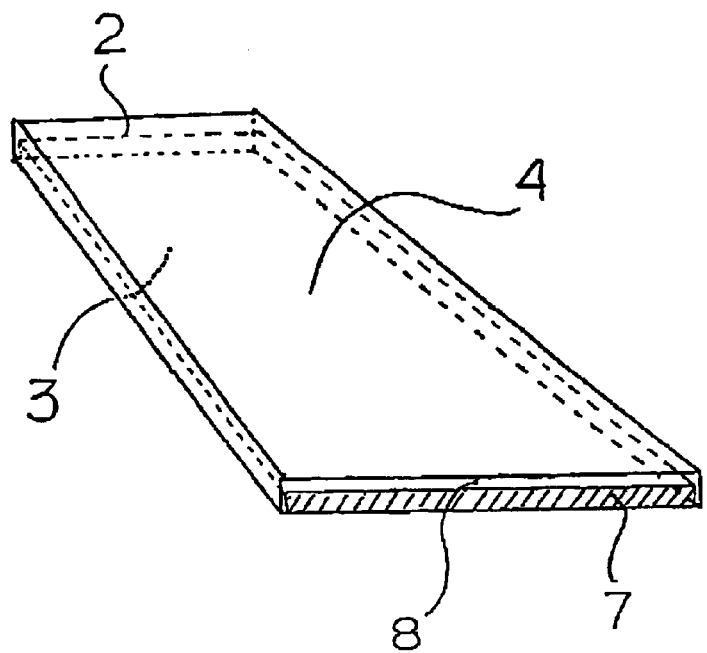

Moreover, when the gas sensor sheet of the invention is used, the indicator housing is preferably loaded with the sheet in such a manner that the stripe pattern of change-color layers will be disposed in parallel with the plane of the opening (gate). For example, when the gas indicator housing shown in FIG. 1 is loaded with the gas sensor sheet shown in FIG. 8, the constituent change-color layers (11)~(14) on the sheet are aligned in parallel with the gate plane. Since, in this arrangement, the individual change-color layers may undergo change in shade one after another according to the gas concentration, exposure time or CT value, the gas detection is further facilitated.

Thus, the gas indicator comprising a housing loaded with a gas sensor sheet in such a manner that the stripe pattern of change-color layers on the sensor sheet is disposed in parallel with the cross-section of the gate (plane of gate) also falls within the scope of the invention.

When the sheet hold means is employed, the gas sensor sheet can be fixedly secured within the housing so that the apparatus can be supplied in large quantities at low cost. Moreover, since an adhesive or the like is not required, the gas sensor sheet will not be degraded in performance so that the desired gas detection can be achieved with greater certainty Furthermore, since the gas sensor sheet of the invention is formed with a stripe pattern of change-color layers, a stepwise indication of the degree of color change can be obtained. Particularly when the gas indicator housing is loaded with the gas sensor sheet in such a manner that the stripe pattern will be in parallel with the cross-section of the gate, the change in shade according to CT can be easily recognized, so that a quantitative gas detection is further facilitated.

EXAMPLES

The following examples and comparative examples illustrate the characteristic features of the present invention. It should, however, be understood that the scope of the invention is by no means limited to these examples.

Production Example 1

An ozone sensor element (ozone sensor sheet) was fabricated. Kent paper was printed with an ozone sensor ink by silk screen printing (150 mesh) to give an ozone sensor sheet for use as the change-color gas sensor element.

The ozone sensor ink mentioned above was prepared by blending the following ingredients evenly using a mixing mill.

Anthraquinone dye (Miketon Fast Red Violet R, product of Mitsui-BASF Dyestuff Co.) . . . 1.68 parts by weight Oil-soluble dye (Valifast Yellow 4120, product of Orient Chemical Industry Co.; C. I. Solvent Yellow 82) . . . 0.84 part by weight Resinous binder (Ethocel 10, product of Dow Chemical Co., an ethylcellulose resin) . . . 6.55 parts by weight Extender (Aerosil R-972, product of Japan Aerosil Co., silica gel) . . . 7.20 parts by weight Cationic surfactant (CA-2150, product of Nikkol Co., cocoalkyltrimethylammonium chloride) . . . 2.06 parts by weight Solvent (Seefozole MG, product of Nippon Shokubai Co.; ethyl-cellosolve) . . . 81.66 parts by weight Example 1

The above sensor element was cut into the sheet for generally shown in FIG. 2 (solid lines) (upper bottom 10 mm, lower bottom 20 mm×70 mm long×0.2 mm thick) and a plate-like transparent housing (made of acrylic resin), shown in FIG. 2 (solid lines) (gate width 10 mm. bottom width 20 mm×70 mm long×5 mm thick), was loaded with the above sheet to assemble an indicator (gas detector). As shown in FIG. 1(b), this Indicator is so designed that the lower inside wall of the plate-like transparent housing is substantially brought into close contact with said sensor element (7), with a clearance between the upper inside wall of the plate-like transparent housing and said sensor element constituting a gas passage space.

Comparative Example 1

Except that the same sensor element was formed into a sheet having the plan view shown in FIG. 2 (dotted lines) (20 mm wide×70 mm long×0.2 mm thick) and the housing shown in FIG. 2 (dotted lines) (20 mm×70 mm 5 mm thick) was used as the plate-like transparent housing, an indicator was fabricated in otherwise the same manner as in Example 1. Then, the relationship of CT to the distance of color change was investigated as in Example 1. The results are shown in Table 1.

Comparative Example 2

Except that the same sensor element was cut into a strip generally having the plan view shown in FIG. 2 (dotted lines) (10 mm wide×70 mm long×0.2 mm thick) and the housing shown in FIG. 2 (dotted lines) (10 mm×70 mm×5 mm thick) was used as the plate-like transparent housing, an indicator was fabricated in otherwise the same manner as in Example 1. Then, the relationship of CT to the distance of color change was investigated as in Example 1. The results are shown in Table 1.

Test Example 1

The gas detection capability of the indicator fabricated in each of the above Examples and Comparative Examples was investigated. Each indicator was exposed to an ozone atmosphere of 20 ppm ozone concentration for 500 minutes and the CT value and the distance of color change were serially monitored. The results are shown in Table 1. The distance of color change Is the distance from the gate toward the bottom of the housing.

TABLE 1

| Exposure time (in minutes) | 5 | 25 | 50 | 100 | 250 | 500 |
|---|---|---|---|---|---|---|
| CT | 100 | 500 | 1000 | 2000 | 5000 | 10000 |
| Example 1 | 7 mm | 15 mm | 20 mm | 25 mm | 40 mm | 50 mm |
| Comparative Example 1 | 12 mm | 25 mm | 60 mm | — | — | — |
| Comparative Example 2 | 4 mm | 7 mm | 11 mm | 14 mm | 19 mm | 23 mm |

It will be apparent if only from Table 1 that the indicator of Comparative Example 1 is high in the detection sensitivity at low CT but because of the very rapid propagation of color change down to the bottom, is incapable of detecting the gas at high CT. The indicator of Comparative Example 2 was poorly sensitive at low CT. In contrast, with the Indicator of Example 1, the degree of change in shade could be clearly ascertained over a broad CT range from a low CT value to a high CT value.

Test Example 2

Except that the ozone concentration of the atmosphere was set to 2000 ppm, the procedure of Test Example 1 was otherwise repeated to investigate the gas detection capabilities of the indicators. With the indicator of Example 1, the degree of change in shade could be clearly ascertained at each CT value. In contrast, with the indicators of Comparative Examples 1 and 2, the CT-dependent degree of change in shade could hardly be ascertained.

Example 2

The appearance (schematic view) of the low-profile gas detector prior to loading with a gas sensor sheet is shown in FIG. 1(a). The low-profile gas detector loaded with a gas sensor sheet is shown in FIG. 1(b). The side elevation view, plan view and cross-section views of the above gas detector are shown in FIG. 4(a) (c-1) and (c-2), respectively.

Figure 6:
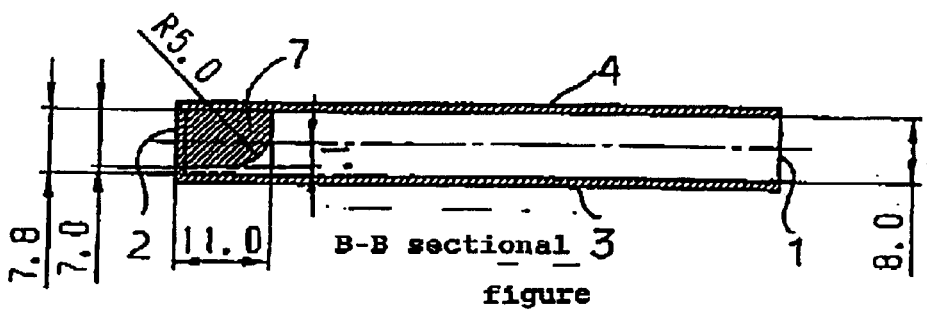
FIG. 6 is a sectional view taken on the line B—B of FIG. 4(b).
Figure 7:
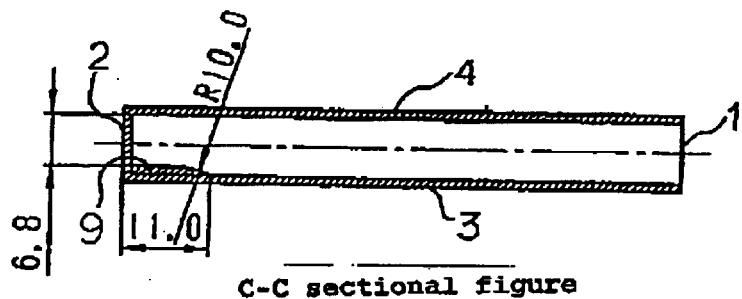
FIG. 7 is a sectional view taken on the line C—C of FIG. 4(b).

This gas detector is a tubular structure consisting of 4 side walls and 2 ends, one of which is open with the other blocked to form a bottom wall. Thus, referring to FIG. 1(a), the indicator comprises an open end (gate) (1), a bottom wall (2) which is farthest from the gate, and said four walls, namely a lower side wall (3), an upper side wall (4) and two lateral side walls (5), (6). Each wall is a planar structure and the area of the cross-section of the indicator which is parallel to the plane of the gate is progressively reduced from the gate to the bottom wall. Thus, the sectional area is minimal at the bottom inside wall (the plane of the deepest part) which is farthest from the gate. The atmosphere (the gas to be detected) enters the gate and flows toward the bottom wall. This housing is made of clear acrylic resin. The walls of the housing can be assembled together using an adhesive or by thermal fusion, or the housing can be formed as a one-piece molding As shown in FIGS. 4~7, this gas indicator is provided with a couple of first projections (9), (9) and one second projection (7) each formed on the inside wall of the gas indicator. The first projections (9), (9) extend from the lower inside wall (3) (FIG. 7). The second projection (7) extends from the upper inside wall (4) (FIG. 6).

Figure 5:
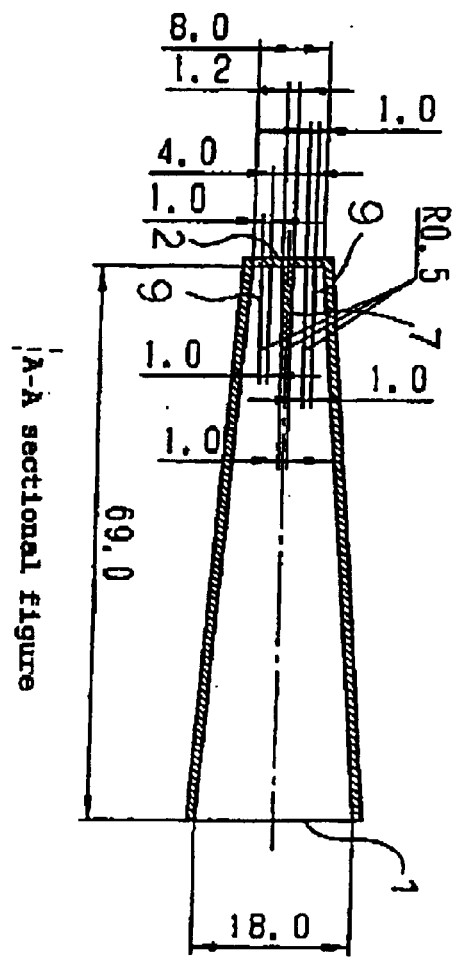
FIG. 5 is a sectional view taken on the line A—A of FIG. 4(c-2).

The two first projections (9), (9) are extending generally perpendicularly from the lower side wall toward the upper side wall (FIG. 5). The apices (crests) of said two first projections are disposed on the base side of the apex of the second projection. On the other hand, the second projection (7) Is extending generally perpendicularly from the upper side wall toward the lower side wall (FIG. 5). The apex (crest) of the second projection is disposed on the base side of the first projections. This tubular indicator is designed so that the length (height) of the first projection (9) is shorter than the length of the second projection (7) in order that the gas sensor sheet may be set in contact (or substantial contact) with the lower inside wall.

Figure 4:
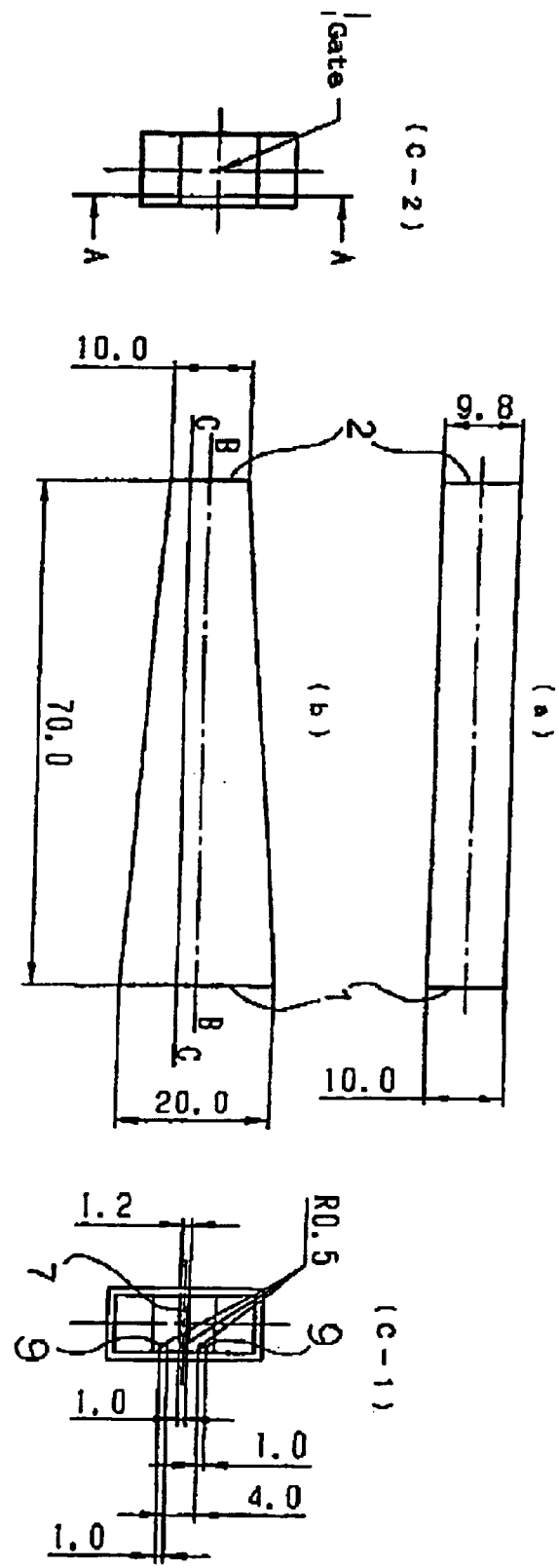
FIG. 4 is a diagrammatic view showing a gas indicator embodying the invention.

As shown in FIG. 4(c-1), the apex of each projection is rounded so as to be free of sharp edges. As the apex is so rounded, the loading and fixation of the gas sensor sheet are facilitated and, moreover, the gas sensor sheet is protected against damage in loading.

FIG. 5 is a sectional view taken on the line A—A of FIG. 4(c-2). The sectional view taken on the line B—B and the sectional view taken on the line C—C of FIG. 4(b) are shown in FIG. 6 and FIG. 7, respectively. It can be seen in FIGS. 5~7 that each projection is a plate-like member extending from the bottom toward the gate of the gas indicator. Each projection may be secured to the upper side wall or lower side wall and the bottom wall.

It can be seen from FIG. 5 that each projection is disposed as extending generally perpendicularly from the bottom wall (2) toward the gate. The side elevation view of each projection is shown in FIGS. 6 and 7. As can be seen from FIGS. 6 and 7, the apex of each projection is rounded in side view so as to be free of sharp edges. By rounding the apex in this manner, the loading with the gas sensor sheet can be further facilitated.

Figure 10:
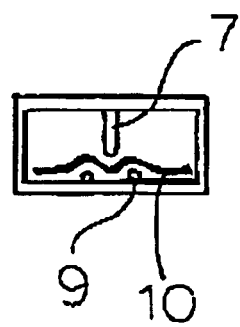
FIG. 10 is a view, corresponding to the cross-section view of FIG. 4(c-1), which shows a gas sensor sheet supported in the sheet-supporting means of the gas detector according to the invention.

Inserted into the indicator housing described above, the gas sensor sheet is fixed in position under the biasing force applied by the two first projections (9), (9) from below and the biasing force applied from above by the opposing second projection (7) which acts between the two points of biasing by said first projections. FIG. 10 shows the interior of the housing as viewed from the bottom toward the gate. As shown in FIG. 10, the gas sensor sheet (10) (cross-sectional view) is supported in a concave fashion and secured generally in contact with the lower inside wall of the housing. In this case, as viewed in the longitudinal direction of the gas indicator, the gas sensor sheet is secured in the vicinity of the bottom wall which is the most remote from the gate.

Figure 12:
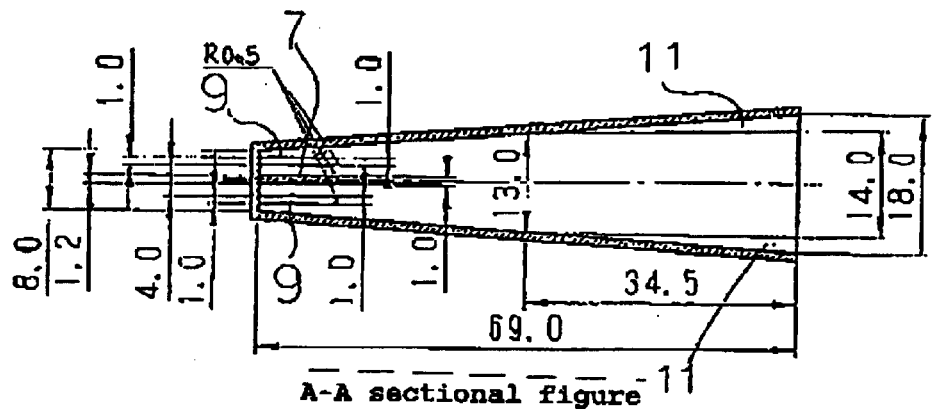
FIG. 12 is a sectional view taken on the line A—A of FIG. 11(c-2).
Figure 13:
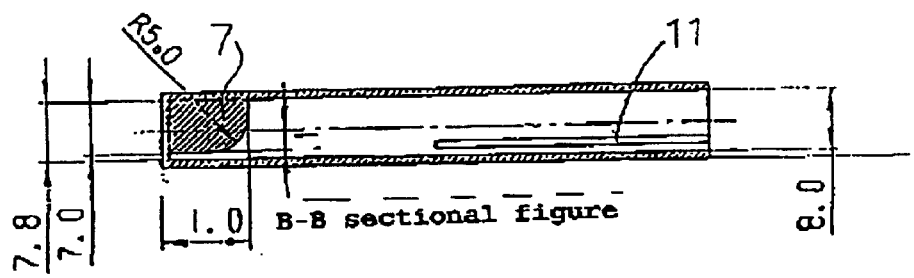
FIG. 13 is a sectional view taken on the line B—B of FIG. 11(b).
Figure 14:
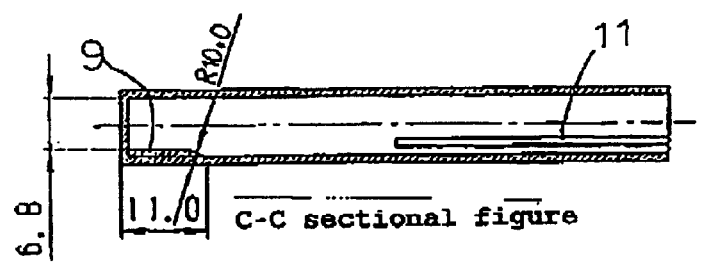
FIG. 14 is a sectional view taken on the line C—C of FIG. 11(b).

In this arrangement, the lateral wall of the housing may also be provided with a projection. An example of the provision of third projections on the lateral sides is shown in FIGS. 11~14. By providing such third projections (11), (11), the loading and fixation of the gas sensor sheet are still further facilitated. As shown in FIGS. 12~14, the third projection can be a plate-like member extending from the gate to the mid-point of the length of the housing.

Figure 15:
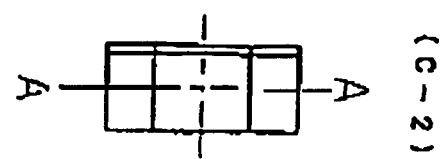
FIG. 15 is a diagrammatic representation of a gas indicator embodying the Invention, FIG. 15(a) Is a side elevation view.
Figure 15:
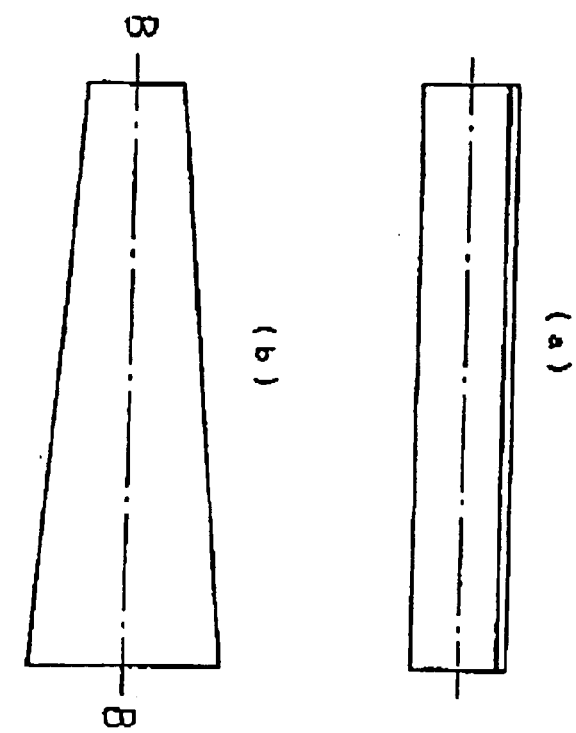
Figure 15:
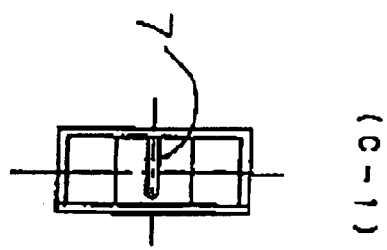
Figure 16:
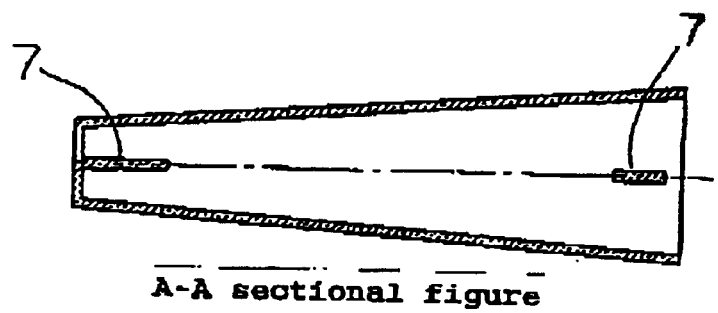
FIG. 16 is a sectional view taken on the line A—A of FIG. 15(c-2).
Figure 17:
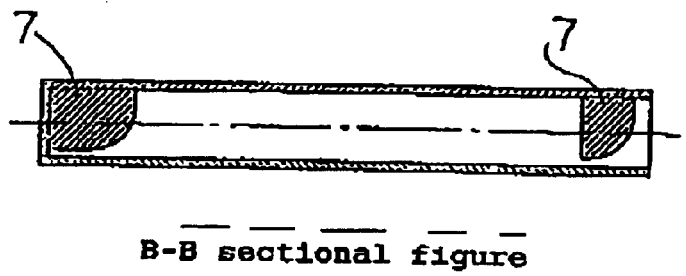
FIG. 17 is a sectional view taken on the line B—B of FIG. 15(b).
Figure 18:
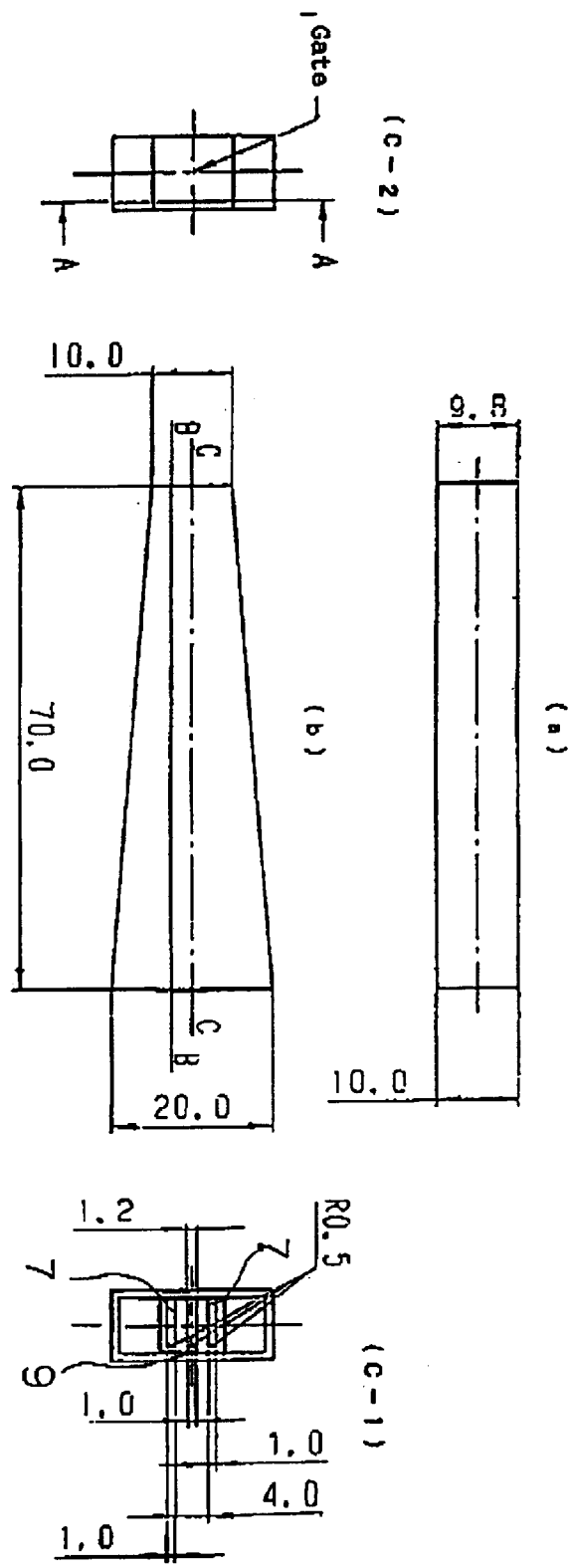
FIG. 18 is a diagram showing a gas indicator embodying the invention.
Figure 19:
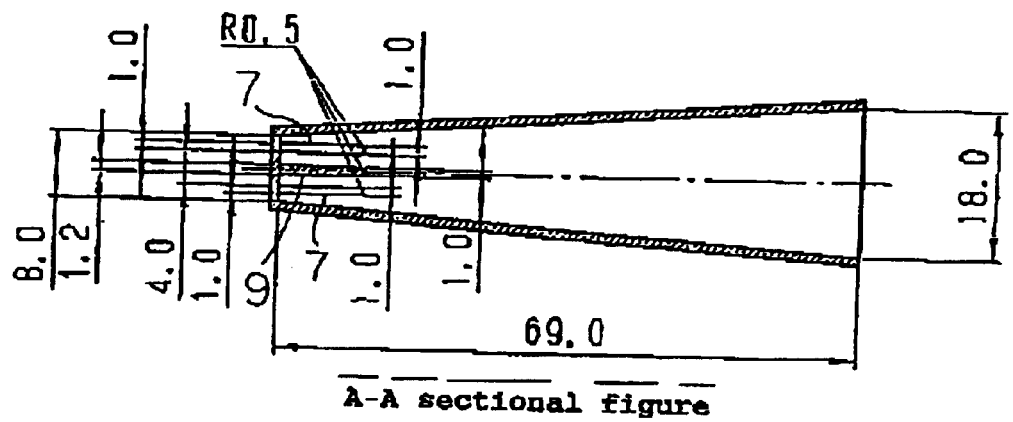
FIG. 19 is sectional view taken on the line A—A of FIG. 18(c-2).
Figure 20:
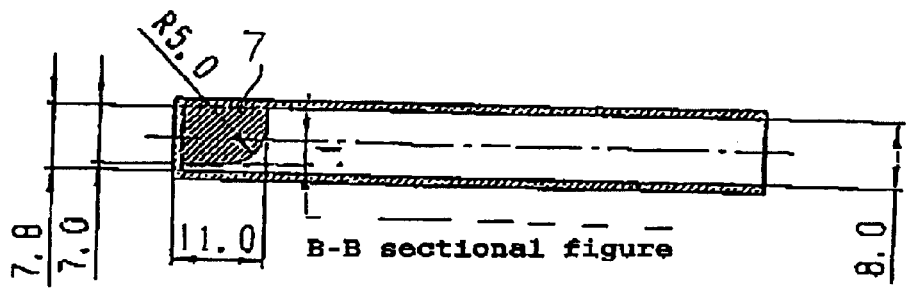
FIG. 20 is a sectional view taken on the line B—B of FIG. 18(b).
Figure 21:
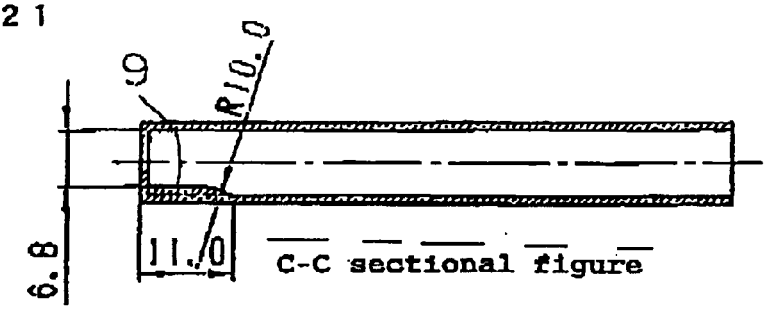
FIG. 21 is a sectional view taken on the line C—C of FIG. 18(b).

The second projection may also be disposed on the upper inside wall close to the gate of the housing in addition to the one disposed on the bottom wall. In this case, as the second projection is disposed on the bottom wall and in the vicinity of the gate as shown in FIGS. 15~17, the first projections and third projections may be omitted.

Further, referring to FIG. 4(c-1), the first and second projections may be reversed. Thus, as shown in FIGS. 18~21, for instance, a first projection (9) is disposed on the lower inside wall and second projections (7). (7) are disposed on the upper inside wall. The second projections are more elongated than the first projection so as to extend down on both sides of the first projection. By this arrangement, the gas sensor sheet can be secured in position with certainty and ease just as in the above case of providing said third projections.

In the present invention, each projection can be molded integrally with the housing proper. An alternative procedure comprises fabricating the housing and each of said projections independently and assembling them with the aid of an adhesive or by thermal fusion.

Test Example 2

Figure 8:
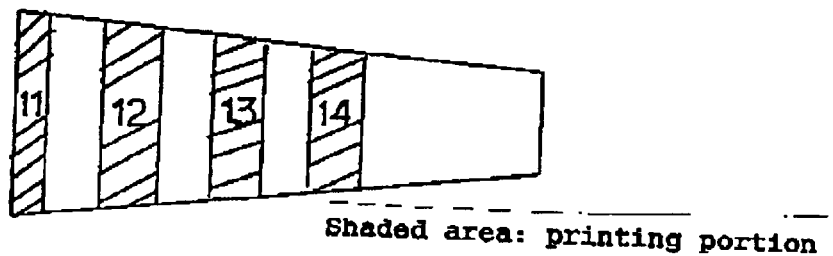
FIG. 8 is a plan view showing the gas sensor sheet used in Example 2.
Figure 9:
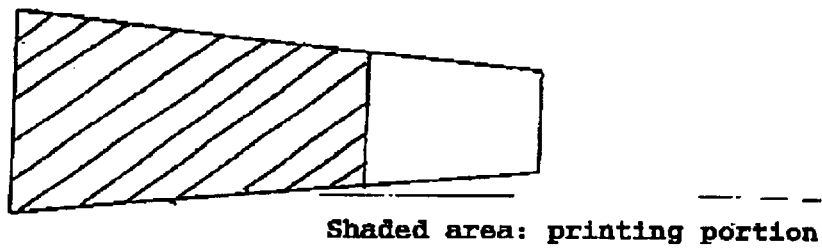
FIG. 9 is a plan view of the gas sensor sheet used in Example 2.

The gas indicator according to Example 1 was loaded with the gas sensor sheet (Kent paper) shown in FIG. 8 or 9 and the detection of ozone gas was attempted.

First, a change-color ink for forming the change-color layer of the gas sensor sheet was prepared. The change-color ink was prepared by blending the following ingredients evenly with a mixing mill: anthraquinone disperse dye (Miketon fast Red Violet R, product of Mitsui-BASF Dyestuff Co.) 1.68 parts by weight; oil-soluble dye (Valifast Yellow 4120, product of Orient Chemical Industry Co.; C. I. Solvent Yellow 82) 0.84 part by weight: resinous binder (Ethocel 10, product of Dow Chemical Co., an ethylcellulose resin) 6.55 parts by weight; extender (Aerosil R-972, product of Japan Aerosil Co.; silica gel) 7.20 parts by weight; cationic surfactant (CA-2150, product of Nikkol Co.; cocoalkyltrimethylammoninm chloride) 2.06 parts by weight; and solvent (Seefozole MG, product of Nippon Shokubai Co.; ethyl-cellosolve) 81.66 parts by weight.

Then, a sheet of Kent paper was printed with the above change-color ink by the silk screen printing technique (150 mesh) to fabricate gas sensor sheets shown in FIGS. 8 and 9. The gas sensor sheet shown in FIG. 8 had a stripe pattern of change-color layers indicated as shaded areas (11)~(14). The gas sensor sheet shown in FIG. 9 had color-change layers additionally in the zones other than change-color layers corresponding to the areas (11)~(14) of FIG. 8.

Each of the gas sensor sheets obtained as above was set in the gas indicator housing of Example 1 (made of acrylic resin) to provide the gas indicator A carrying the gas sensor sheet of FIG. 8 or the gas indicator B carrying the gas sensor sheet of FIG. 9. Particularly, the sheet of FIG. 8 was set with its change-color layer (11) in a position adjacent to the gate, with the stripe pattern of change-color layers (11)–(14) being disposed in parallel with the gate.

Each of the above gas indicators was exposed to an ozone-containing atmosphere (ozone concentration 2 ppm) and the CT-dependent change-color performance of the change-color zone was monitored The results are shown in Table 2.

TABLE 2

| CT  | 100 | 500 | 1000 | 2000 |
|-----|-----|-----|------|------|
| (A) | Definite color change in shaded area 1 only | Definite color change down to shaded area 2 | Definite color change down to shaded area 3 | Definite color change down to shaded area 4 |
| (B) | Color change by about 1 mm | Color change by about 5–6 mm | Color change by about 8–12 mm | Color change by about 14–18 mm |

It will be apparent from Table 2 that the zone of color change expanded with increasing CT for both indicators, indicating that ozone can be quantitatively detected with whichever of these Indicators. Particularly in the case of the gas indicator A carrying the gas sensor sheet having a stripe pattern of change-color layers, the change in shade could be confirmed more clearly as compared with the gas indicator (B).

What is claimed is:

1. A gas indicator comprising a change-color gas sensor element and a plate-shaped housing loaded with the change-color gas sensor element, wherein the housing comprises an open end, a closed end, and walls connecting the open end and the closed end, wherein a gas passage space is formed extending from the open end to the closed end over the change-color gas sensor loaded on a plane passing through the open end and the closed end, said housing having a cross-sectional area perpendicular to an axis passing through the open end and the closed end, which cross-sectional area is continuously reduced substantially from the open end to the closed end.

2. The gas indicator according to claim 1 wherein the housing is provided with a transparent window through which a change in shade of the change-color gas sensor element can be ascertained from outside the indicator.

3. The gas indicator according to claim 1 wherein the open end of the housing is formed with a notch.

4. A method of determining the concentration of a gas which comprises disposing the gas indicator of claim 1 in a given atmosphere and determining the CT value from the color difference or color change area resulting from a change in shade of the change-color layer of the gas sensor sheet.

5. The gas indicator according to claim 1, wherein a shape from the open end to the closed end of the housing is trapezoidal.

6. The gas indicator according to claim 1, wherein the change-color gas sensor element is loaded in the housing substantially from the open end to the closed end.

7. The gas indicator according to claim 6, wherein the housing has a rectangular lateral cross section perpendicular to the axis passing through the open end and the closed end, and the change-color gas sensor element is loaded substantially from one side wall of the housing to the other side wall opposite to the one side wall of the housing.

8. The gas indicator according to claim 1 wherein the change-color gas sensor element is a gas sensor sheet which comprises a change-color layer formed from a gas sensor ink on a substrate.

9. The gas indicator according to claim 8 wherein the gas sensor ink contains an anthraquinone dye having at least one of a primary amino group or a secondary amino group.

10. The gas indicator according to claim 8 wherein the gas sensor ink further contains an extender.

11. The gas indicator according to claim 8 wherein the gas sensor ink further contains a binder.

12. The gas indicator according to claim 8 wherein the gas sensor ink further contains a color component which is not altered in shade in an ozone-containing atmosphere.

13. The gas indicator according to claim 8 wherein the gas sensor ink further contains a cationic surfactant of a quaternary ammonium salt type.

14. The gas indicator according to claim 13 wherein the cationic surfactant of the quaternary ammonium salt type is an alkyltrimethylammonium salt.

15. The gas indicator according to claim 8 wherein the sheet hold means is comprised of two or more projections extending from an inside wall of the housing, said projections being disposed in mutually opposed relation to support the gas sensor sheet therebetween.

16. The gas indicator according to claim 15 wherein apices of the mutually opposed projections are displaced from each other, and an apex of one projection projects into a lower position than an apex of the other projection to support the gas sensor sheet between the displaced apices.

17. The gas indicator according to claim 15 wherein one of the mutually opposed projections is shorter than the other projection so that the gas sensor sheet may be supported in the vicinity of the lower inside wall of the housing.

18. The gas indicator according to claim 8 wherein the gas sensor sheet is supported by a sheet hold means provided internally of the housing.

19. The gas indicator according to claim 18 wherein a lower inside wall of the housing is provided with a couple of first projections, and an opposite upper inside wall of the housing is provided with one second projection which is longer than each of the first projections, wherein (a) apices of said first projections are positioned lower than apex of said second projection, (b) said gas sensor sheet is supported in the vicinity of said lower inside wall of the housing which is provided with said first projections, (c) said second projection is located between portions of said gas sensor sheet pressed by said couple of first projections, and (d) each of said first projections and said second projections is shaped like a plate extending from the closed end toward the open end of the housing.

20. The gas indicator according to claim 18 wherein the change-color layer of the gas sensor sheet is formed in a stripe pattern which is parallel to the cross-section of the open end.

21. The gas indicator according to claim 18 wherein the sheet hold means is comprised of one or more projection extending from an inside wall of the housing.

22. The gas indicator according to claim 21 wherein the projection is a planar member extending from the closed end toward the open end of the housing.

23. The gas indicator according to claim 21 wherein the projection is a planar member extending from the closed end toward the open end of the housing, said planar projection being secured to the lateral inside wall of the housing as well.

* * * * *